(12) United States Patent
Parthasaradhi Reddy et al.

(10) Patent No.: US 7,732,632 B2
(45) Date of Patent: Jun. 8, 2010

(54) PROCESS FOR OBTAINING PURE OSELTAMIVIR

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 147 days.

(21) Appl. No.: 11/719,773

(22) PCT Filed: Jan. 2, 2006

(86) PCT No.: PCT/IN2006/000001
§ 371 (c)(1),
(2), (4) Date: May 21, 2007

(87) PCT Pub. No.: WO2007/077570
PCT Pub. Date: Jul. 12, 2007

(65) Prior Publication Data
US 2009/0149670 A1    Jun. 11, 2009

(51) Int. Cl.
*C07C 229/48*    (2006.01)

(52) U.S. Cl. .................................................. 560/125
(58) Field of Classification Search ................ None
See application file for complete search history.

(56) References Cited

U.S. PATENT DOCUMENTS
2004/0180933 A1    9/2004    Brown et al.

FOREIGN PATENT DOCUMENTS
WO    WO9807685 A1    2/1998

OTHER PUBLICATIONS

John C. Rohloff, et al. Practical Total Snythesis of the Anti-Influenza Drug GS-4104, J. Org. Chem. 1998, 63, 4545-4559, Glead Sciences Inc. Process Chemistry, 353 Lakeside Drive, Foster city, California 94404, Received Feb. 23, 1998.
PCT Notification of Transmittal of The International Search Report and The Written Opinion of the International Searching Authority, or the Declaration.

*Primary Examiner*—Paul A Zucker
(74) *Attorney, Agent, or Firm*—Caesar, Rivise, Bernstein, Cohen & Pokotilow, Ltd.

(57) ABSTRACT

The present invention provides a process for obtaining highly pure crystalline form of oseltamivir free base, thus, for example, suspending or dissolving impure or non-crystalline oseltamivir free base in a hydrocarbon solvent and then isolating crystals to obtain oseltamivir free base in well defined crystalline form. The present invention also provides a process for preparation of oseltamivir phosphate in high purity.

11 Claims, 1 Drawing Sheet

PROCESS FOR OBTAINING PURE OSELTAMIVIR

FIELD OF THE INVENTION

The present invention provides a process for obtaining highly pure crystalline form of oseltamivir free base. The present invention also provides a process for preparation of oseltamivir phosphate in high purity.

BACKGROUND OF THE INVENTION

U.S. Pat. No. 5,763,483, which is herein incorporated by reference, disclosed carbocyclic compounds and pharmaceutically acceptable salts thereof. Among them Oseltamivir, chemically Ethyl (3R,4R,5S)-4-(acetylamino)-5-amino-3-(1-ethylpropoxy)-1-cyclohexene-1-carboxylate is a orally active inhibitor of influenza virus neuraminidase. Oseltamivir is represented by the following structure:

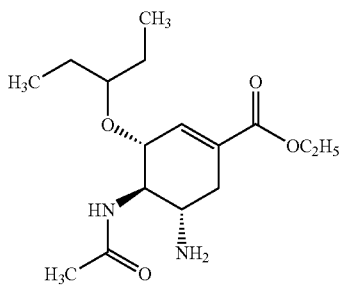

Various processes for preparation of oseltamivir and its pharmaceutically acceptable salts were disclosed, for example, in U.S. Pat. No. 5,763,483, J. Org. Chem., Vol. 63, No. 13, 1998 (page: 4545-4550), J. Amer. Chem. Soc., Vol. 115, No. 4, 1997 (Page: 681-690), U.S. Pat. No. 5,952,375, PCT Publication No. WO 98/07685 and PCT Publication No. WO 99/44185.

PCT Publication No. WO 98/07685 described in example 11 that crystalline oseltamivir free base is obtained by concentrating reaction mass containing oseltamivir free base to obtain oseltamivir free base as a foam, which is solidified on standing. It has been found that the process described in WO 98/07685 does not produce the well-defined crystalline form of oseltamivir free base in a consistently reproducible manner.

Oseltamivir free base obtained by these processes are not satisfactory from purity point of view and there is a need for a process for obtaining consistently reproducible pure crystalline oseltamivir free base.

One object of the present invention is to provide a process for preparation of highly pure crystalline oseltamivir free base that can be used to obtain pharmaceutically acceptable salts of oseltamivir in high purity.

Another object of the present invention is to provide a process for preparation of oseltamivir phosphate in high purity.

DETAILED DESCRIPTION OF THE INVENTION

According to one aspect of the present invention, there is provided a process for isolation of pure crystalline oseltamivir free base, the said process comprises suspending or dissolving impure or non-crystalline oseltamivir free base in a hydrocarbon solvent and then isolating crystals to obtain oseltamivir free base in well defined crystalline form.

The crystalline oseltamivir free base obtained by the process as described in the present invention is characterized by an x-ray powder diffraction spectrum having peaks expressed as $2\theta$ at about 4.8, 5.2, 6.9, 8.7, 9.9, 10.5, 11.9, 13.0, 14.5, 17.2, 17.3, 18.4, 18.6, 19.9, 21.0, 21.3, 22.2, 22.5, 23.9 and 24.7 degrees as shown in FIG. 1.

Preferable hydrocarbon solvent is selected from the group consisting of n-hexane, n-heptane, cyclohexane, toluene, xylene and a mixture thereof. More preferable hydrocarbon solvent is n-heptane, toluene or a mixture thereof.

Preferably the suspension is stirred for at least 30 minutes at below boiling temperature of the solvent used, more preferably for 1 hour to 4 hours at 15-60° C. and still more preferably for 1 hour to 3 hours at 20-40° C.

The isolation of the crystalline oseltamivir free base may be carried out by usually known methods such as filtration or centrifugation.

The isolation may, if required, be carried out by cooling, seeding, partial removal of the solvent from the solution, by adding an anti-solvent to the solution or a combination thereof.

According to another aspect of the present invention, there is provided a process for preparation of pure oseltamivir phosphate, the said process comprises by contacting a solution or suspension of an organic acid addition salt of oseltamivir with a solution of phosphoric acid in an alcoholic solvent and then isolating pure oseltamivir phosphate from the solution.

The solution or suspension of the organic acid addition salt of oseltamivir used in the above process is prepared by dissolving or suspending the organic acid addition salt of oseltamivir in a ketonic solvent or an alcoholic solvent or a mixture thereof.

Preferable ketonic solvent is selected from the group consisting of acetone, methyl ethyl ketone, methyl isobutyl ketone, methyl isopropyl ketone, methyl tert-butyl ketone and more preferable ketonic solvent is acetone; preferable alcoholic solvent is selected from the group consisting of methanol, ethanol, isopropyl alcohol, tert-butyl alcohol and more preferable alcoholic solvent is ethanol.

The organic acid addition salt of oseltamivir is prepared by dissolving oseltamivir free base in an ester solvent or a ketonic solvent, adding an organic acid to the solution and then isolating organic acid addition salt of oseltamivir from the solution.

Preferable ester solvent is selected from the group consisting of ethyl acetate, methyl acetate, isopropyl acetate, tert-butyl methyl acetate, ethyl formate and more preferable ester solvent is ethyl acetate; preferable ketonic solvent is selected from the group consisting of acetone, methyl ethyl ketone, methyl isobutyl ketone, methyl isopropyl ketone, methyl tert-butyl ketone and more preferable ketonic solvent is acetone.

Preferable organic acid is selected from the group consisting of tartaric acid, dibenzoyl tartaric acid, di-p-toluoyl tartaric acid, 10-camphorsulfonic acid, lactic acid, malic acid, mandelic acid, citric acid, fumaric acid, maleic acid, succinic acid, methane sulfonic acid and p-toluenesulfonic acid. More preferable organic acid is tartaric acid.

The process ensures the high purity oseltamivir. The process of the invention has the advantage that oseltamivir phosphate obtained has the better purity than when prepared by usual method of converting oseltamivir free base directly to oseltamivir phosphate by using phosphoric acid. The process of the invention has also the advantage in that oseltamivir phosphate obtained has the better purity than when prepared by neutralizing a salt of oseltamivir, isolating oseltamivir free base and converting the free base to oseltamivir phosphate.

'Impure' in the specification refers to having HPLC purity 98% or less and 'pure' refers to having HPLC purity more than 98%.

Figure 1:
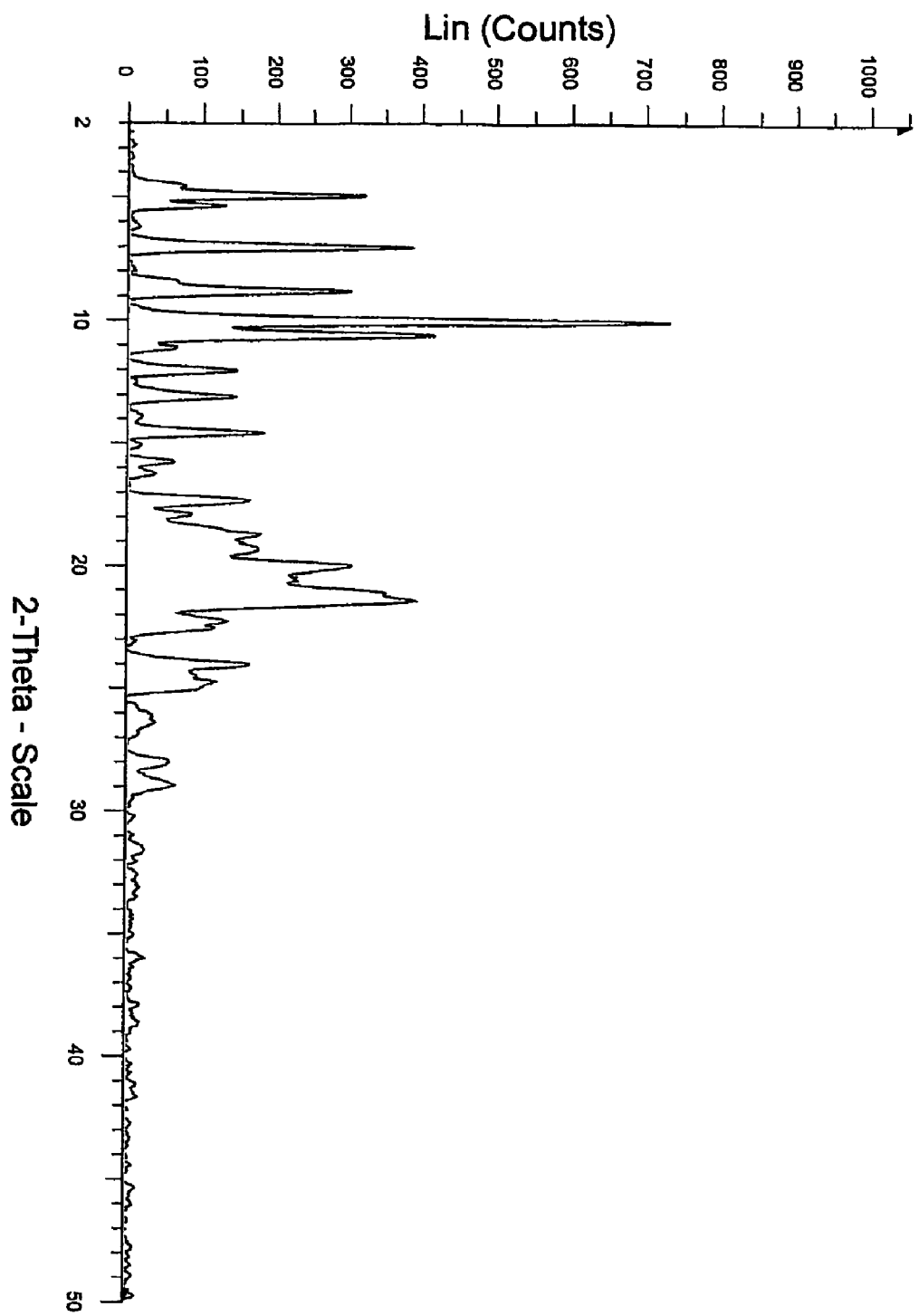
FIG. 1 is a x-ray powder diffraction spectrum of crystalline oseltamivir free base obtained in example 1.

X-ray powder diffraction spectrum was measured on a Bruker axs D8 advance x-ray powder diffractometer having a Copper-Kα radiation. Approximately 500 mg of sample was gently flattened on a sample holder and scanned from 2 to 50 degrees two-theta, at 0.03 degrees two-theta per step and a step time of 0.5 seconds. The sample was simply placed on the sample holder. The sample was rotated at 30 rpm at a voltage 40 KV and current 35 mA.

The invention will now be further described by the following non-limiting examples.

EXAMPLE 1

Step-(a):

Oseltamivir phosphate (20 gm, HPLC purity: 97%) is stirred with water (100 ml) and methylene chloride (100 ml) for 10 minutes at 25-30° C. and then pH of the mass is adjusted to 9-10 with liquor ammonia. Separated the layers, the organic layer is subjected to carbon treatment and filtered on hiflo bed. Washed the hiflo bed with methylene chloride (20 ml) and then distilled the organic layer under vacuum at 40° C. to give 16.5 gm of oseltamivir free base as a residue.

Step-(b):

To the residue obtained in step-(a) is added n-heptane (100 ml) and stirred for 1 hour at 25-30° C. Filtered the solid and dried to give 13 gm of pure oseltamivir free base (HPLC Purity: 99.2%, Melting Range: 102.5-103.9° C.).

EXAMPLE 2

The residue (5 gm, obtained as per the process described in step-(a) of example 1) is dissolved in toluene (10 ml), n-heptane (70 ml) is slowly added to the solution for 30 minutes to 1 hour at 20-30° C. and then stirred for 2 hours at 20-30° C. Filtered the solid, washed with n-heptane (20 ml) and dried to yield pure oseltamivir free base (HPLC Purity: 99.3%).

EXAMPLE 3

Tartaric acid (5 gm) is added to the solution of oseltamivir free base (9 gm, HPLC purity: 95.8%) in ethyl acetate (50 ml) at 25-30° C., the contents are heated to 50° C. and then slowly cooled to 30° C. in 1 hour. Filtered the solid, washed with 70 ml of ethyl acetate and dried to yield 13 gm of oseltamivir tartrate (HPLC purity: 97.2%).

EXAMPLE 4

Oseltamivir tartrate (13 gm, obtained in example 3) is added to acetone (150 ml) at 25-30° C., the solution of $H_3PO_4$ (3.5 gm) in 40 ml of ethanol is added to the contents and then stirred for 1 hour 30 minutes at 25-30° C. Filtered the solid, washed with 30 ml of acetone and dried to yield 6.5 gm of oseltamivir phosphate (HPLC purity: 99.8%).

Without further elaboration of the foregoing will so fully illustrate our invention that others may, by applying current or future knowledge, adapt the same for use under various conditions of service.

We claim:

1. A process for preparation of pure oseltamivir phosphate, which comprises contacting a solution or suspension of an organic acid addition salt of oseltamivir with a solution of phosphoric acid in an alcoholic solvent and then isolating pure oseltamivir phosphate from the solution.

2. The process as claimed in claim 1, wherein the solution or suspension of the organic acid addition salt of oseltamivir is prepared by dissolving or suspending the organic acid addition salt of oseltamivir in a ketonic solvent or an alcoholic solvent or a mixture thereof.

3. The process as claimed in claim 2, wherein the ketonic solvent is selected from the group consisting of acetone, methyl ethyl ketone, methyl isobutyl ketone, methyl isopropyl ketone and methyl tert-butyl ketone; and the alcoholic solvent is selected from the group consisting of methanol, ethanol, isopropyl alcohol and tert-butyl alcohol.

4. The process as claimed in claim 3, wherein the ketonic solvent is acetone.

5. The process as claimed in claim 3, wherein the alcoholic solvent is ethanol.

6. The process as claimed in claim 1, wherein the organic acid addition salt of oseltamivir is prepared by dissolving oseltamivir free base in an ester solvent or a ketonic solvent, adding an organic acid to the solution and then isolating the organic acid addition salt of oseltamivir from the solution.

7. The process as claimed in claim 6, wherein the ester solvent is selected from the group consisting of ethyl acetate, methyl acetate, isopropyl acetate and tert-butyl methyl acetate, ethyl formate; and the ketonic solvent is selected from the group consisting of acetone, methyl ethyl ketone, methyl isobutyl ketone, methyl isopropyl ketone and methyl tert-butyl ketone.

8. The process as claimed in claim 7, wherein the ester solvent is ethyl acetate.

9. The process as claimed in claim 7, wherein the ketonic solvent is acetone.

10. The process as claimed in claim 1, wherein the organic acid is selected from the group consisting of tartaric acid, dibenzoyl tartaric acid, di-p- toluoyl tartaric acid, 10-camphorsulfonic acid, lactic acid, malic acid, mandelic acid, citric acid, fumaric acid, maleic acid, succinic acid, methane sulfonic acid and p-toluenesulfonic acid.

11. The process as claimed in claim 10, wherein the organic acid is tartaric acid.

* * * * *